(12) United States Patent
Ahmed et al.

(10) Patent No.: US 8,778,694 B2
(45) Date of Patent: Jul. 15, 2014

(54) BATCH METHODS FOR ENRICHING TRACE IMPURITIES IN HYDROGEN GAS FOR THEIR FURTHER ANALYSIS

(75) Inventors: Shabbir Ahmed, Naperville, IL (US); Sheldon H. D. Lee, Willowbrook, IL (US); Romesh Kumar, Naperville, IL (US); Dionissios D. Papadias, Chicago, IL (US)

(73) Assignee: Uchicago Argonne, LLC, Chicago, IL (US)

( * ) Notice: Subject to any disclaimer, the term of this patent is extended or adjusted under 35 U.S.C. 154(b) by 517 days.

(21) Appl. No.: 12/835,614

(22) Filed: Jul. 13, 2010

(65) Prior Publication Data

US 2011/0005302 A1    Jan. 13, 2011

Related U.S. Application Data

(60) Provisional application No. 61/224,968, filed on Jul. 13, 2009.

(51) Int. Cl.
*G01N 33/00* (2006.01)

(52) U.S. Cl.
CPC .................................. *G01N 33/0014* (2013.01)
USPC ............................................. 436/144; 436/56

(58) Field of Classification Search
None
See application file for complete search history.

(56) References Cited

U.S. PATENT DOCUMENTS 7,690,241 B2    4/2010    Muntz

OTHER PUBLICATIONS

Lu et al. "Inorganic membranes for hydrogen production and purification: A critical review and perspective", J. Coll. Interface Sci., 2007, v. 314, pp. 589-603.*

Jack et al., "CO2 Capture Using Dense Hydrogen Transport Membranes", Sixth Annual Conference on Carbon Capture & Sequestration, May 2007, http://www.search-document.com/pdf/1/2/2010-dense-membranes-hydrogen-production.html.*

"Hydrogen Transport Membrane (HTM) for Separation of Pure Hydrogen at High Temperatures" (Argonne National Lab, no date) http://web.anl.gov/techtransfer/pdf/HTM_RandD.pdf.*

J. T. Keurentjes, et al., High-Flux Palladium Membranes Based on Microsystem Technology; Industrial Engineering Chemistry Research 2004, 43, pp. 4768-4772.

A. Basile, et al., A Dense Pd/Ag Membrane Reactor for Methanol Steam Reforming. Experimental study. Catalyst Today 2005, 104, pp. 244-250.

(Continued)

*Primary Examiner* — Yelena G Gakh

(74) *Attorney, Agent, or Firm* — Cherskov Flaynik & Gurda, LLC

(57) ABSTRACT

Provided herein are batch methods and devices for enriching trace quantities of impurities in gaseous mixtures, such as hydrogen fuel. The methods and devices rely on concentrating impurities using hydrogen transport membranes wherein the time period for concentrating the sample is calculated on the basis of optimized membrane characteristics, comprising its thickness and permeance, with optimization of temperature, and wherein the enrichment of trace impurities is proportional to the pressure ratio $P_{hi}/P_{lo}$ and the volume ratio $V_1/V_2$, with following detection of the impurities using commonly-available detection methods.

18 Claims, 12 Drawing Sheets

(56) References Cited

OTHER PUBLICATIONS

N. Itoh, et al., Preparation of Thin Palladium Composite Membrane Tube for a CVD Technique and Its Hydrogen Permselectivity. Catalysis Today 2005, 104, pp. 231-237.

R.W. Baker, Membrane Technology and Applications in McGraw Hill 2000, pp. 297-298.

D. Papadias, et al., Hydrogen Quality for Fuel Cell Vehicles—A Modeling Study of the Sensitivity of Impurity Content in Hydrogen to the Process Variables in the SMR-PSA System, International Journal of Hydrogen Energy 34, pp. 6021-6035, 2009.

J. Hille, Enrichment and Mass Spectrometic Analysis of Trace Impurity Concentrations in Gases (1990) Journal of Chromatography, 502 (2), pp. 265-274.

Alfred Pebler, et al., Cryogentics Applied to Mass Trace Gas Analysis, Analytical Chemistry, vol. 45, No. 2, Feb. 1973.

H.J. Rath, et al., Wacker-Chemitronic Gesellschaft fur Electronic-Grundstoffe mbH, Postfach 1140, D-8263 Burghausen, Federal Republic of Germany, Accepted May 11, 1980.

\* cited by examiner

Schematic of a Dual-Chamber H₂ Quality Membrane Gas Sampling and Enrichment Device Schematic of a Dual-Chamber H₂ Quality Membrane Gas Sampling and Enrichment Device where Heat is Applied Directly to the Membrane Schematic of a Dual-Chamber $H_2$ Quality Membrane Gas Sampling and Enrichment Device Test System. TC=Thermocouple Procedure of a H₂ Quality Adsorbent Gas Sampling and Enrichment Device Hydrogen Quality Adsorbent Gas Sampling and Enrichment Device Containing Two Vessels in Series, Chamber 1 Contains the Adsorbent and Chamber 2 is an Empty Vessel. Analysis of Enriched Gas is Analyzed from Chamber 2.

a) Working Load of adsorbent at Varying Pressure
b) Schematic Representation of a Bed During Adsorption and Desorption of Species A+B Error in Single Component Enrichment (CO=2 ppm) when the Feed Mixture Also Contains Other Species of Varying Concentration ($N_2$, $CO_2$ and $CH_4$) in the Hydrogen Gas. For a total impurity Concentration of i.e. 602 ppm (CO=2 ppm, $N_2$=$CO_2$=$CH_4$=200 ppm). When the Total Impurity Concentration is 0 ppm, the Mixture Contains Only CO at 2 ppm in Hydrogen.

Enrichment of Single Component Mixture in Hydrogen ($N_2/H_2$, $CO/H_2$, $CH_4/H_2$, $CO_2/H_2$ and $H_2S/H_2$) on activated carbon. The diluted species at various concentrations in the feed is adsorbed at 20 atm (280 psig) and concentrated during Desorption to a Final Pressure of 1.1 atm (1.5 psig)

CO Enrichment Factor on Activated Carbon as Function of Feed Pressure (0-4400 psig). Desorption Pressure = 1.1 atm.

Impurity concentrations in the hydrogen before and after the enrichment process using the adsorption system. The total gas flow of 200 L was sufficient to equilibrate the 24 g of sorbent with all four impurity species.

BATCH METHODS FOR ENRICHING TRACE IMPURITIES IN HYDROGEN GAS FOR THEIR FURTHER ANALYSIS

PRIORITY

This utility application claims the benefits of U.S. Provisional Patent Application No. 61/224,968, filed on Jul. 13, 2009, the entirety of which is incorporated by reference.

CONTRACTUAL ORIGIN OF THE INVENTION

The U.S. Government has rights in this invention pursuant to Contract No. DE-AC02-06CH11357 between the U.S. Department of Energy and UChicago Argonne, LLC, as operator of Argonne National Laboratory.

BACKGROUND OF THE INVENTION

1. Field of the Invention

The invention relates to the field of detection of impurities in a fluid. Specifically, the invention relates to an apparatus and method that facilitates the detection of minimal quantities of impurities in hydrogen fuel through concentration of the impurities by a known amount and subsequent measurement of the concentrated impurities. When coupled with an appropriate detector or sensor, the device can provide quantitative analysis (or concentrations) of the impurities in the original sample gas.

2. Background of the Invention

Fuel cell and other hydrogen fueled vehicles are slated for commercial deployment in the US and around the world. A number of demonstration hydrogen refueling centers have been set up around the US. Several teams of vehicle manufacturers and fuel suppliers have worked with state and federal government[1,2] in the demonstration of hydrogen refueling centers where the hydrogen is dispensed at the nozzle at elevated pressure (5,000-10,000 psig) into a vehicle's hydrogen storage tanks. Since fuel cells are very sensitive to gases like carbon monoxide, hydrogen sulfide, ammonia, etc., the fuel supplier must ensure that the concentrations of these species are limited to suggested guidelines. Examples of these guideline values suggested by the Society of Automotive Engineers (SAE) are shown in Table 1, and show that the limits on CO, $NH_3$ and sulfur are extremely low and that they are at, or very close to, the detection limits of standardized analytical methods.

TABLE 1

SAE suggested guideline values for the maximum allowable concentrations for impurities in hydrogen for fuel cell vehicles.

| | |
|---|---|
| Hydrogen, minimum | 99.97% |
| Impurities & Limits | Maximum |
| (Excluding helium, must be <100 ppm) | |
| Helium (He) | 300 ppm |
| Nitrogen (N2) + Argon (Ar) | 100 ppm |
| Total Hydrocarbons (HC) (C1 basis) | 2 ppm |
| Carbon Dioxide (CO2) | 2 ppm |
| Carbon Monoxide (CO) | 0.2 ppm |
| Ammonia (NH3) | 0.1 ppm |
| Sulfur (S, as H2S, COS, etc.) | 0.004 ppm |

$H_2$ suppliers (stations) will need to meet these specifications and certify the purity of the product they dispense.

Hydrogen-generation plants currently at the demonstration refueling centers operate at conservative operating conditions to ensure the desired quality of hydrogen. The gas dispensed to the vehicles is periodically sampled and analyzed using customized analytical methods and sophisticated equipments. Organizations such as the ASTM are developing new standardized methods for the analysis of hydrogen for fuel cells.

Meanwhile, the current practice is to harvest samples periodically and send the samples to analytical laboratories, where the fluids are analyzed. State of the art instrumentation is required, such as, for example, a gas chromatograph fitted with a pulse discharged helium ionization detector (GC/PDHID) to analyze for carbon monoxide at concentrations of 0.2 parts per million or lower, or a gas chromatograph fitted with a sulfur chemiluminescence detector (GC/SCD) to analyze for total sulfur species. These sensitive instruments are expensive, and they require considerable laboratory time of skilled analytical chemists.

The high cost of these analyses can be borne by the demonstration projects because of the large intervals between gas samples. However, with the larger deployment of fuel cell vehicles and the anticipated growth in the refueling infrastructure in the years ahead, refueling stations will have to conduct more frequent and rapid analysis and/or monitoring of the key species, using simpler and inexpensive technologies. Some of the key factors that necessitate the development of new analytical technology for analysis of hydrogen are:

Standardized methods for analysis of the trace species have not been defined and validated.

Current methods require the use of expensive equipment that can cost in excess of $100,000 per unit and are not suited for on-site analysis. Indeed, the pressures at which hydrogen is to be stored at refueling stations is much higher than state of the art current hydrogen sampling methods which operate at no more than atmospheric pressures, and usually less.

Current methods require considerable time and skilled operators.

Current analytical methods can add 4-10 cents/kg to the cost of hydrogen.

A need exists in the art for an in-situ apparatus and method to determine contaminant levels in hydrogen fuels. The apparatus and method should not require costly analytical tools or elaborate protocol so as to allow their use by minimally trained personnel at vehicle refilling stations. The apparatus and method should be operable at hydrogen gas pressures much higher than atmospheric pressure, and typically operable at pressures at which hydrogen gas is commercially stored.

SUMMARY OF INVENTION

An object of the invention is to provide an apparatus and method to facilitate the quantitative analysis of impurities in fluids. A feature of this invention is the concentration or enrichment of trace impurities within fluid samples. An advantage of the invention is that it allows for measuring of the quality of fluid without the use of highly sensitive and expensive equipment.

Another object of the invention is to facilitate the detection of contaminants in hydrogen gas that can damage a fuel cell. A feature of the invention is that it is capable of enriching impurity concentrations. An advantage of the invention is that it facilitates detection of low levels of trace species, such as $H_2S$, $CO_2$, $NH_3$, and CO, in fuel, while the fuel is maintained at pressures above atmospheric pressure, and before the fuel containing the species contacts the fuel cell. When combined with a detector, the invention provides an in situ signal point to move any fuel, which contains higher than allowable contaminant levels, to off line status.

Another object of the invention is to provide an apparatus and method to facilitate the analysis of hydrogen fuel on site of a vehicle fuel dispensing station. A feature of the instant invention is that the enrichment and analysis tools (detectors, sensors, etc.) may be located within a single portable unit. Another feature of the invention is that it is capable of storing enriched sample until analysis of the sample is required. An advantage of the instant invention is that it can provide indications of fuel quality within 2-60 minutes.

Yet another object of the instant invention is to provide an automated device for enriching impurities of a fuel to facilitate the determination of fuel quality. A feature of the invention is that with the enrichment device combined with a detector, the measurements can occur without user intervention. Inasmuch as the device provides a means for storing the enriched impurities, measurements of impurities can take place at regular scheduled intervals, or simultaneous with the production of the enriched aliquots. An advantage of the invention is that the combination (enrichment device and detector) can provide an in situ indication of fuel quality prior to dispensing of fuel and can prevent dispensing of fuel if contaminants in the fuel exceed certain levels.

Briefly, a method for enriching impurities in a sample is provided, comprising sequestering the sample in at least one analytical chamber wherein the sample contains a predominant gas and an unknown quantity of trace impurities; increasing the concentrations of trace impurities relative to the predominant gas; and measuring the total quantity of trace impurities. The measuring of the concentrated impurities can be facilitated by a detector in fluid communication with the invented process.

Also provided is a device for enriching impurities in a hydrogen gas stream, the device comprising a first container adapted to receive the stream; a means for removing only the hydrogen gas from said container while retaining the impurities in the container; and a means for measuring the retained impurities.

The invention also provides a device for measuring and enriching impurities in a hydrogen stream, the device comprising: a container for receiving the stream; an adsorbent positioned within said container, whereby the adsorbent reversibly sequesters the impurities; a means of egress adapted to allow removal of hydrogen gas from the container while keeping said adsorbent in said container; and a means for removing and measuring the impurities from said adsorbent.

Also provided is a device for measuring impurities in a hydrogen stream, the device comprising a container for receiving the stream; an adsorbent positioned within said container, whereby the adsorbent reversibly sequesters the impurities; a means of egress adapted to allow removal of hydrogen gas from the container while keeping said adsorbent in said container; and a means for removing and measuring the impurities from said adsorbent. Exemplary adsorbents include, but are not limited to activated carbon, carbon molecular sieves, various zeolites, silica gel, alumina, and combinations thereof.

BRIEF DESCRIPTION OF THE DRAWINGS

The invention together with the above and other objects and advantages will be best understood from the following detailed description of the preferred embodiment of the invention shown in the accompanying drawings, wherein.

DETAILED DESCRIPTION OF THE INVENTION

Figure 1A:
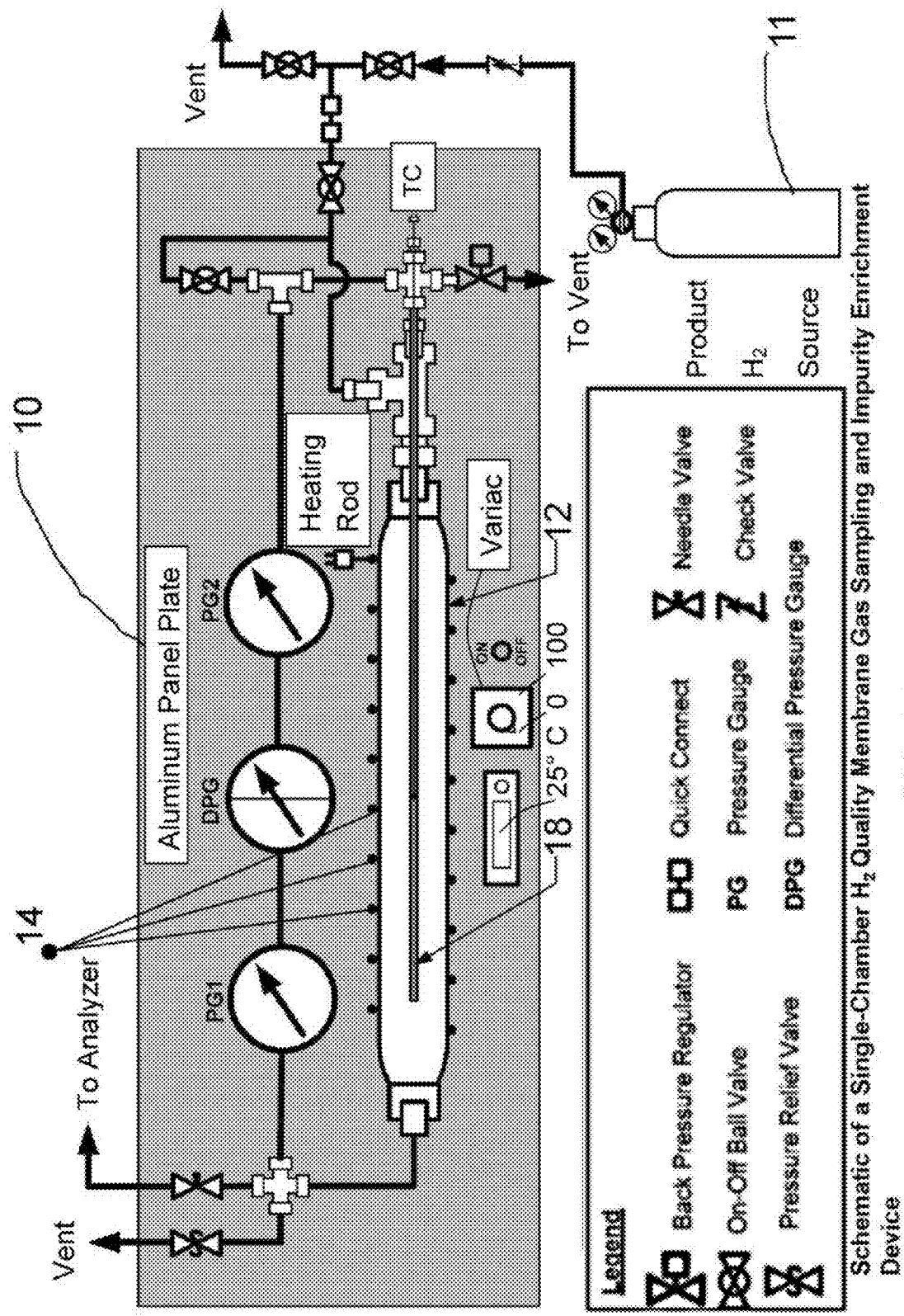
FIGS. 1A-D depict schematics of four embodiments of a membrane-based impurity enriching gas sampler.

The foregoing summary, as well as the following detailed description of certain embodiments of the present invention, will be better understood when read in conjunction with the appended drawings.

The invention facilitates the determination of concentrations of trace components in hydrogen by enriching the impurities in the gas sample. Two embodiments of the invention are as follows: 1) Hydrogen Removal, and 2) Impurity Enrichment by Adsorption.

Each method and associated apparatus features a separate sample processing (impurity concentration) protocol which will include the time, temperature, pressure, and flow parameters. The embodiments are focused on the analysis of trace species that are of concern for low temperature (i.e., between about 40° C. and 200° C.) polymer electrolyte fuel cells; specifically those species ($H_2S$, CO, $NH_3$ etc) which poison the fuel cell, and those species ($CH_4$, $N_2$ He, Ar, etc) which dilute the hydrogen, all of which lead to a lowering of the efficiency of the fuel cell. However, the methods described herein may be used with any contaminant of a fluid.

Hydrogen Removal
Protocol Detail

FIGS. 1A-D depict embodiments of the invention whereby impurity concentrations are increased to easily detectable levels (i.e., between 100 ppb and 100 ppm) by removing known volumes of the fluid. For example, hydrogen in a gas sample is removed from a closed system, thereby increasing the relative concentrations of impurities in the sample left behind. The hydrogen exits the system via one or more hydrogen-transport membranes, while the impurities remain. The process comprises:

a. Collecting the sample (e.g., hydrogen with trace impurities) at an elevated pressure ($P_{hi}$) (i.e., within a range of about 100 and 12000 psi) in a sampling device. The device, defining a closed environment, contains a membrane that selectively permeates hydrogen and any moiety not considered detrimental to the power system. For example, if neat hydrogen is the ultimate feedstream, a palladium-containing membrane is a suitable membrane constituent.

b. Allowing the hydrogen to permeate out until the sample chamber pressure is reduced to a lower pressure ($P_{lo}$)

c. Analyzing the un-permeated gas to determine the type and amount of the impurities present in the un-permeated gas.

In one embodiment, the concentration of the impurities in the chamber (at $P_{lo}$) are multiplied by a factor of $P_{hi}/P_{lo}$. A ratio of 50:1, for example, wherein the initial or first sample pressure is 50 times that of a final or second sample pressure, results in a 50-fold "increase" in contaminant concentrations. Specifically, collecting a sample at 1,000 psia at the nozzle, permeating the hydrogen out to a final pressure of 20 psia, results in increasing the concentration of the impurities by a factor of 50. Consequently, if the hydrogen dispensed at the feed nozzle contained 4 parts per billion (ppb) $H_2S$, its concentration in the final sample will be raised to 200 ppb. This increase in concentrations allows for the use of less sensitive detection devices such as portable or handheld detectors to make final concentration determinations.

Transport membranes are at the core of this impurity enrichment method. In one embodiment of the invention, wherein the purity of hydrogen gas is at issue, palladium membranes are utilized of the type and in the protocols described in Keurentjes, J. T. F.; Gielens, F. C.; Tong, H. D.; van Rijn, C. J. M.; Vorstman, M. A. G., High-Flux Palladium Membranes Based on Microsystem Technology. Industrial and Engineering Chemistry Research 2004, 43, 4768-4772; Basile, A.; Gallucci, F.; Paturzo, L., A dense Pd/Ag membrane reactor for methanol steam reforming: Experimental study. Catalysis Today 2005, 104, 244-250; Itoh, N.; Akiha, T.; Sato, T., Preparation of thin palladium composite membrane tube by a CVD technique and its hydrogen permselectivity. Catalysis Today 2005, 104, 231-237, and Baker, R. W., Membrane Technology and Applications. In McGraw-Hill, pp. 297-298: 2000, all of which are incorporated herein by reference.

The hydrogen permeation through Pd-based membranes follow a 5-step mechanism:

1) Sorption of hydrogen molecules on the metal surface;
2) Dissociation of hydrogen molecules into hydrogen atoms on the metal surface;
3) Each hydrogen atom loses its electron to the metal lattice and diffuses through the lattice as an ion;
4) Re-association of hydrogen atoms and electrons emerging at the permeate side of the membrane surface to form hydrogen molecules; and
5) Desorption of hydrogen molecules from the metal surface to complete the permeation process.

At temperatures above 200° C., the surface sorption and dissociation of hydrogen molecules are fast; therefore, the hydrogen permeation rate is controlled by the diffusion of hydrogen ions through the metal lattice and can be characterized by both Sievert's and Arrhenius' laws (Eq. 1):

$$J = \frac{\Phi_0}{l_m} e^{(-E/RT)} \left[ \sqrt{P_{H_2,hi}} - \sqrt{P_{H_2,lo}} \right] \quad \text{Equation 1}$$

where J is the hydrogen flux, $P_{H_2,hi}$ is hydrogen pressure in the gas phase, $P_{H_2,lo}$ is hydrogen pressure on the permeate side of the membrane, $\phi_o$ is the frequency factor, E is the apparent activation energy for rate of hydrogen transport through the Pd membrane and $I_m$ the thickness of the membrane metallic layer. At temperatures below 200° C., the sorption and dissociation of hydrogen molecules on the membrane surface control the rate of hydrogen transport, and the permeation characteristics of the membrane deviate from Sievert law. Equation 1 shows that the membrane's hydrogen flux is a function of the membrane temperature, membrane metallic layer thickness and the pressures imposed across the membrane.

For hydrogen membrane separation processes, the selective metallic membrane layer is designed to be extremely thin to achieve economical hydrogen fluxes, generally varying from about 1 micron up to 100 microns, depending on the application temperature and pressure. Exemplary membrane thicknesses range from about 1 micron to 50 microns.

To improve the strength and reduce the cost, composite membranes are used. In these devices, a thin Pd-alloy layer is deposited onto a micro-porous ceramic or base-metal layer by electrolytic coating, vacuum sputtering, or chemical vapor deposition. The choice of membrane preparation method depends on many factors, such as the nature of the metal, required membrane thickness and surface area, geometric form, and purity.

Suitable hydrogen permeation membranes operate most efficiently at elevated temperatures (i.e., greater than about 175-200° C.), including palladium-alloy membranes as discussed herein. Alternatively, non-palladium membranes can be used. At these temperatures, undesired reactions such as methanation reactions ($3H2+CO \rightarrow CH4+H2O$) may be catalyzed by the nickel and iron found as constituents of stainless steel sampling vessels. Preferably, embodiments of the invention have reaction chambers and tanks lined with fused silica. Tests in the laboratory have confirmed that fused silica linings inhibit undesirable reactions such as the methanation reactions discussed supra. Reactions are further limited with the use of a combination of fused silica linings and lower operating temperatures. Generally, conformal linings which are substantially continuous, and blemish free provide the best results for minimizing secondary reactions.

Undesirable carbon-producing side reactions (such as $2CO \rightarrow CO_2 + C$, $CO + H_2 \rightarrow C + H_2O$) can occur on the metal surfaces, leading to reduced permeability of hydrogen. Tests with high (0.2-2.5%) concentrations of CO and high temperatures, i.e, above 350 C, have confirmed this phenomenon. This CO-consuming reaction can be inhibited by lowering the temperature of the chamber and/or the membrane and also lowering the time at elevated temperatures. This can be achieved through a combination of thinner membranes and larger permeation surface area. Thus, such combination provides a means for maintaining permeability of hydrogen through the membrane. This combination also preventing inadvertent consumption of CO which would otherwise lead to the incorrect conclusion that less CO exists in the sample.

Sulfur species ($H_2S$) in hydrogen can poison the palladium surface and lead to a rapid decline in hydrogen permeability. This poisoning effect is overcome by using palladium-alloys (i.e., palladium alloyed with gold, copper, silver, etc.)

A feature of the invention is that it provides a batch process, not a continuous process for enriching and analyzing impurities in a high pressure hydrogen fluid. It comprises a multi-chamber apparatus to enable permeation through thin membranes (e.g., membranes from about 1 to about 10 microns in thickness, and preferably from about 1 to about 5 microns) at low pressure differentials. Such differentials are between 20 and 50 psig. Thicker membranes (e.g., membranes greater than about 10 microns and typically between about 30 to 50 microns) will accommodate pressure differentials of up to approximately 1000 psig. All of the impurities are enriched equally in that the enrichment factor is identical for all impurity species.

The membrane-containing reaction chamber embodiments are depicted in FIGS. 1A-D. Each of these embodiments includes a heating element to increase the temperature of a membrane 18. In a first embodiment of the invented system, designated as numeral 10, and shown in FIG. 1A, an impurity concentrating vessel 12 also serves as a sample retaining vessel adapted to receive hydrogen gas as produced at commercial production facilities 11. Heating of the vessel 12 occurs along substantially its entire exterior. Specifically, the heating elements 14 are circumferentially disposed along longitudinally extending exterior surfaces of the chamber.

Figure 1B:
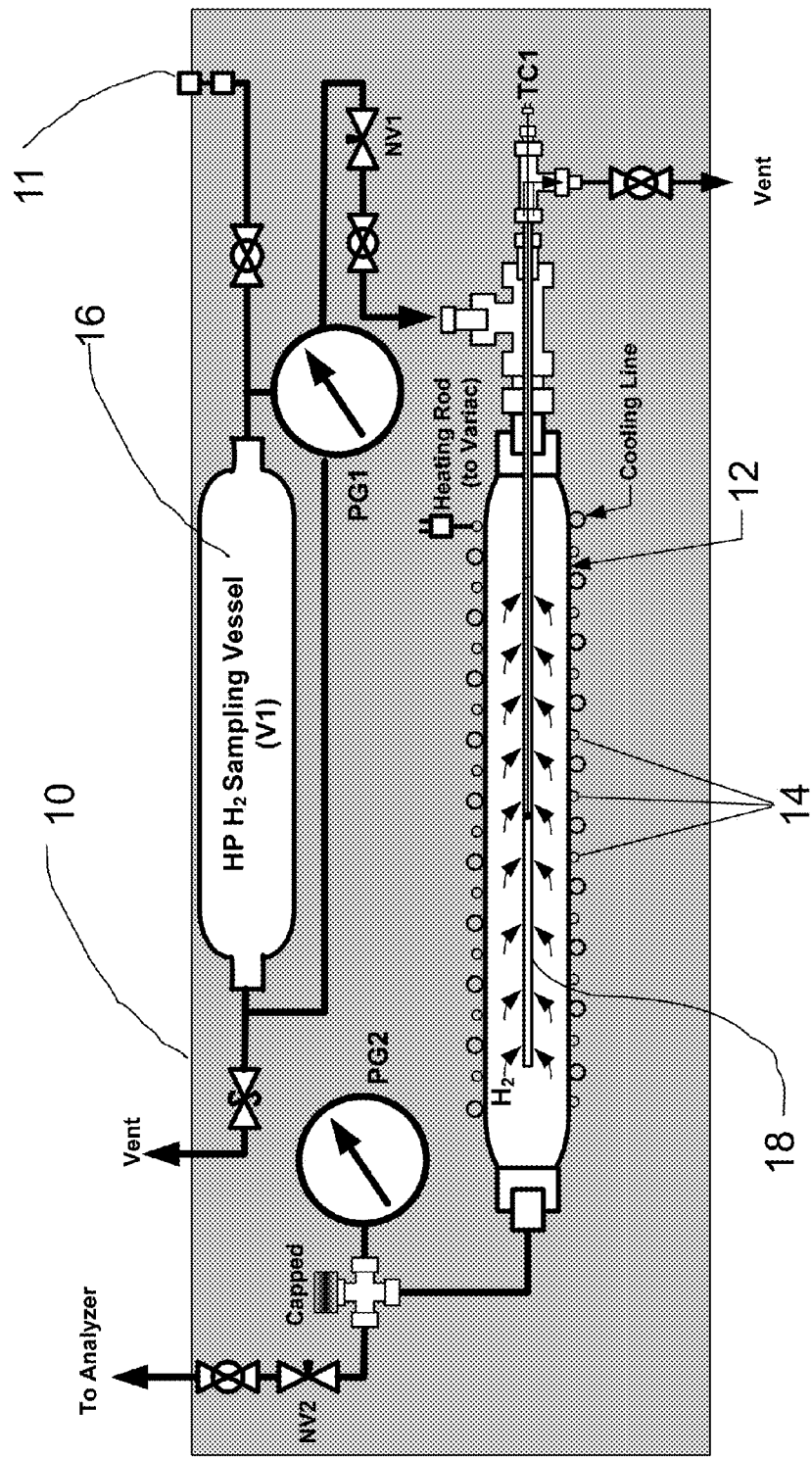
Figure 1C:
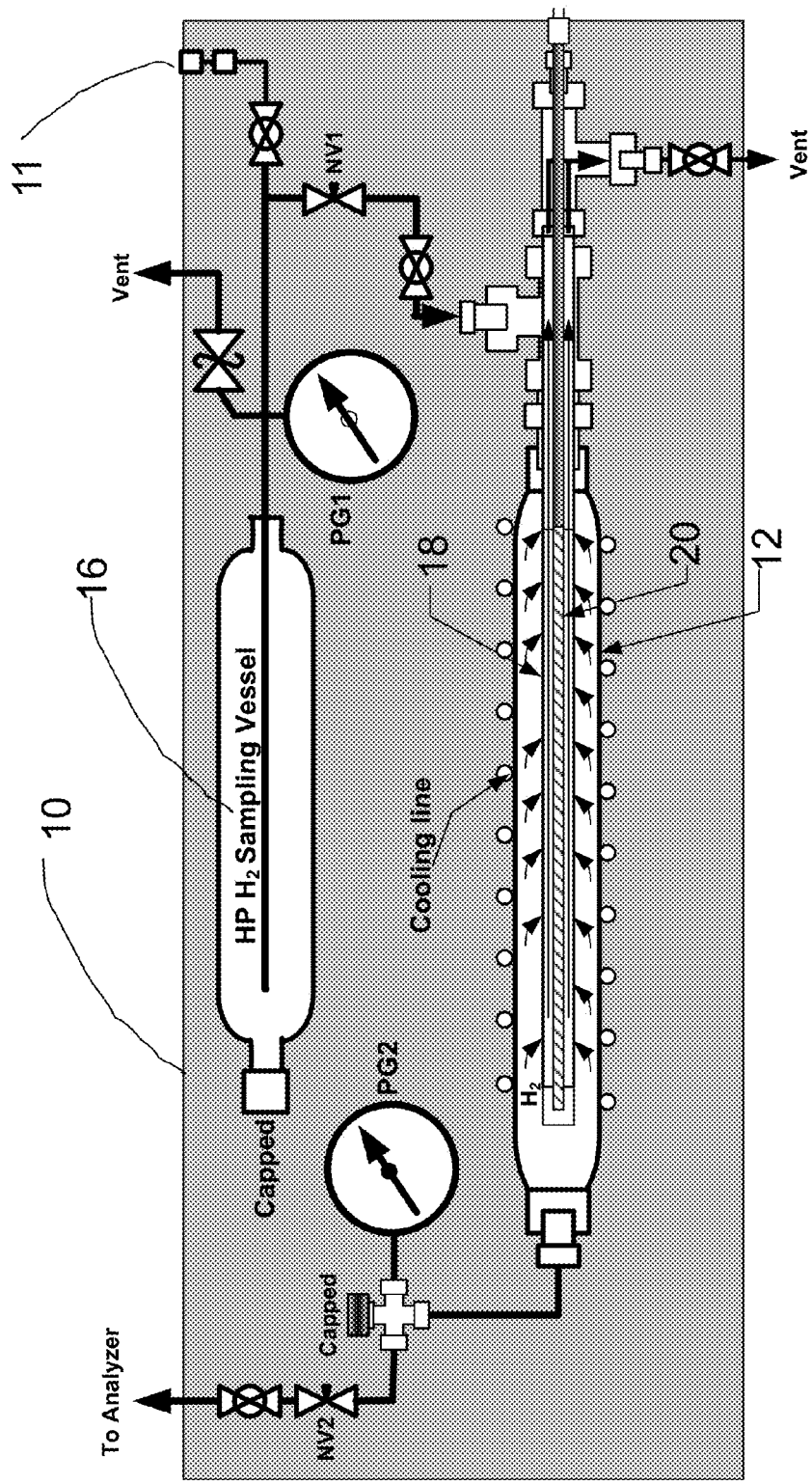
Figure 1D:
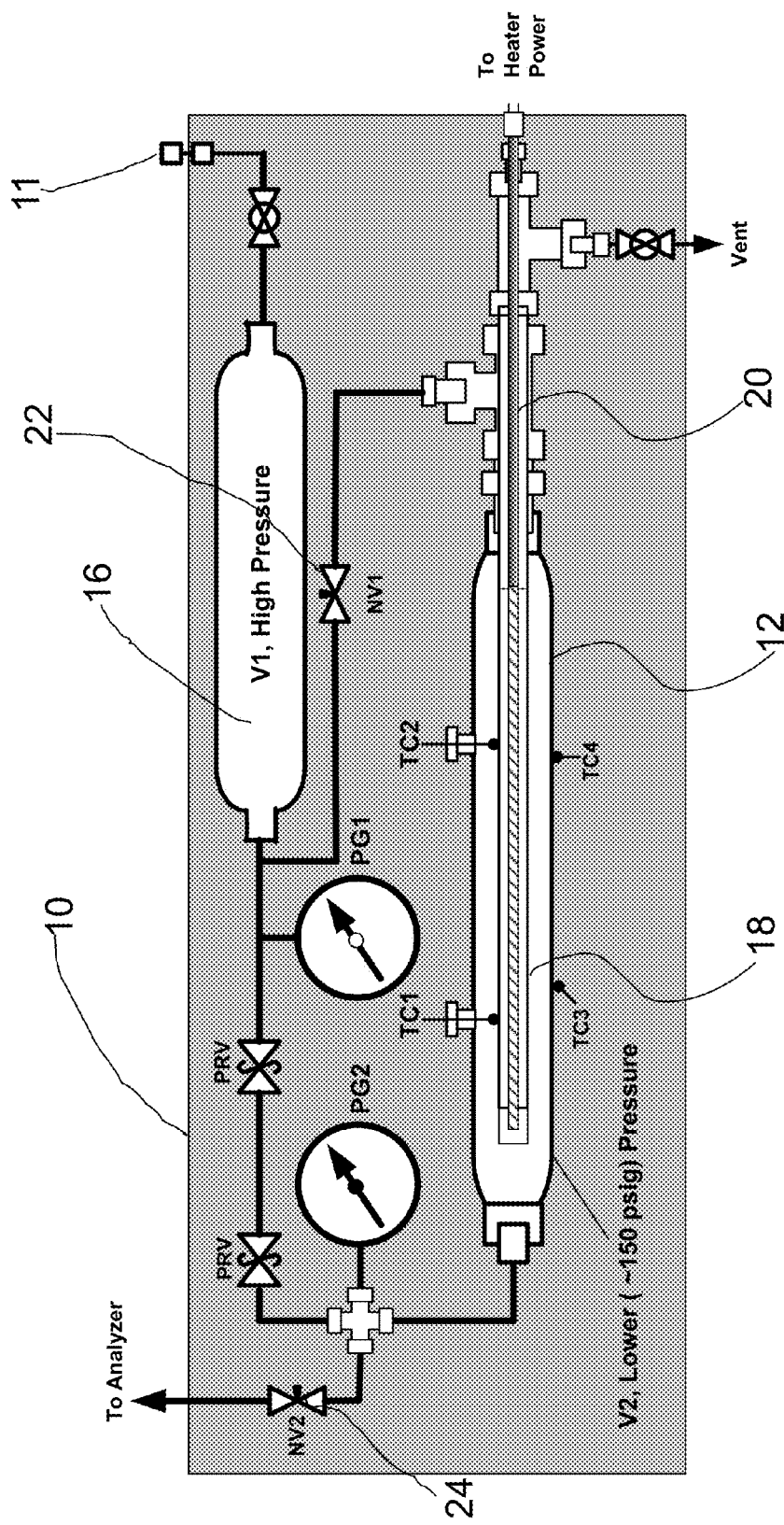

In the alternative embodiments shown in FIG. 1B-D, a separate sample retaining vessel 16 exists for the storage of the sample at a high pressure. This retaining vessel is physically separate, but in fluid communication with, the impurity concentrating vessel 14 such that this embodiment provides two defined voids. The provision of the two chambers or voids eliminates the need to heat the entire void representing the reaction chamber and also eliminates the need to heat the entire sample to activation temperature of the membrane.

FIG. 1C depicts an embodiment wherein only the membrane 18 is heated by a heating element 20 disposed along an interior, longitudinally extending core of the membrane so as to be in physical contact with interior surfaces of the membrane. As such, an interior of the membrane defines a cavity adapted to receive a rod-shaped heating element, or other type of elongated heating core. In this embodiment, the membrane encapsulates a heating means.

Alternatively, the membrane surface can also be resistively heated. The membrane metallic layer can hence serve as a heating element and temperature controlled by varying the amount of current that flows through the layer.

FIG. 1D also depicts the method of using the apparatus. The method is divided into two phases: concentration of impurities followed by regeneration of apparatus.

Concentration step 1. The system 10 is flushed/purged with hydrogen 11 to be analyzed. Then, the sample retention chamber 16, designated as volume one (V1) is charged at high pressure (P1=1000 to 12000 psig) with target fuel fluid.

Concentration step 2. Actuating a valve 22 placed intermediate the sample retention container 16 (i.e., volume one, V1), and the impurity concentration container 12, causes the fuel fluid to flow to the concentration container 12. In the concentration container (i.e. volume two, V2), the fuel fluid is maintained at a second pressure (P2) (wherein P2<P1). Suitable P2 pressures range from about 10 to 1000 psig, preferably from 20 psig to 300 psig and most preferably from 40 psig to 250 psig. P2 is maintained while $H_2$ permeates through the heated membrane (>150° C.) membrane 18. Certain polymeric membranes do not require heating at high temperature and therefore can be maintained at between 20° C. and 150° C. As such, a feature of the invention is that it removes hydrogen through a membrane with minimal pressure difference between the two sides of the membrane. Also, no carrier gas is required to be removed inasmuch as no carrier gas is present.

Concentration step 3. When P1 is less than 50 psig, the intermediate valve 22 is closed and the impurity concentrating vessel 12 is allowed to cool.

Concentration step 4. Inject impurity-concentrated gas from the impurity concentrating vessel 12 into an analyzer through a second fluid control valve 24 which is disposed intermediate V2 and the analyzer.

Regeneration step 1. Flow pure hydrogen or hydrogen sample gas 11 air through the entire sample device 10 with the valves substantially open while slowly heating the membrane 18 to between 150 and 300° C., for t1 minutes Regeneration step 2. Cool the membrane 18.

Hydrogen Flux Through

Metallic Membranes Detail

An important parameter quantifying the membrane 18 operation is the hydrogen flux, J, that describes the number of hydrogen molecules permeating as function of time, unit membrane area, temperature, and pressure differential. For high enough temperatures (where the dissociation/reassociation reactions are fast) and for relatively thick membranes (>10 μm), the rate limiting step is the diffusion of hydrogen atoms in the metal. The diffusion of hydrogen through a metal phase can be described with Fick's first law Equation 2 as a function of concentration gradient and diffusion coefficient, D:

$$J = D \frac{\partial C}{\partial x} \qquad \text{Equation 2}$$

Sievert's law, Equation 3, may be used to describe the relationship of the concentration of hydrogen atoms on the metal surface to the pressure of hydrogen in the gas-phase, $$C = K_S \sqrt{P_{H_2}} \qquad \text{Equation 3}$$

where the square-root relationship of the hydrogen pressure is due to the dissociation of $H_2$ molecules into two hydrogen atoms. The combination of Equations 2 and 3 and considering that two hydrogen atoms are transferred per molecule of hydrogen the hydrogen flux can be expressed as Equation 4, to with:

$$J = \frac{K_S D}{2} \frac{\left[\sqrt{P_{H_2,hi}} - \sqrt{P_{H_2,lo}}\right]}{l_m} \qquad \text{Equation 4}$$

where $I_m$ is the thickness of the membrane. The term $0.5 K_S D / I_m = \phi$, the permeance of the membrane, has been found to vary with temperature in an Arrhenius type of relationship. A more general expression for the flux is Equation 5, below:

$$J = \Phi_0 e^{(-E/RT)} \sqrt{\Delta P_{H_2}} \qquad \text{Equation 5}$$

Equation 5 correlates the flux for different pressures and temperature and it is useful for design purposes. The permeability will vary dependant on the metal surface, and the activation energy will dictate how low the temperature can be before the dissociation/reassociation reactions start to limit the permeation rates.

With the use of Equation 5, the time required to concentrate a sample can be calculated and can also provide a relationship to use for optimization. Moreover, if an explicit expression can be derived, the expression can be used for control purposes as well. Assuming that that the impurities in the sample are low enough, the partial pressure of hydrogen can be approximated with the total pressure in the sampling device. For diffusion of hydrogen in the Pd membrane being the rate limiting process, the hydrogen flow, $N_{H2}$ as function of time is a first order differential equation, to wit, Equation 6:

$$N_{H2} = \frac{\partial n_{H2}}{\partial t} = \left(\frac{V}{RT}\right)\frac{\partial P_{H2}}{\partial t} = -\left(\frac{\Phi_0}{l_m}e^{(-E/RT)}\right)A_m\left(\sqrt{P_{retentate}} - \sqrt{P_{permeate}}\right) \quad \text{Equation 6}$$

where V and T are the impurity concentration vessel 12 volume and temperature respectively, $\phi$ the permeance of the membrane and $A_m$ is the membrane surface area. Retentate and permeate are the gases on the high pressure and low pressure sides of the membrane. By integrating Equation 6, the time necessary to reduce the retentate pressure from an initial sampling pressure ($P_{initial}$) to a final pressure ready for sampling ($P_{final}$) is given by Equation 7, below:

$$t = \left\{\sqrt{P_{permeate}}\ln(P_{initial} - P_{permeate}) - \right.$$
$$2\sqrt{P_{initial}} + 2\sqrt{P_{permeate}}\operatorname{arctanh}\left(\sqrt{\frac{P_{initial}}{P_{permeate}}}\right) - $$
$$\sqrt{P_{permeate}}\ln(P_{final} - P_{initial}) + 2\sqrt{P_{final}} - $$
$$\left.\sqrt{P_{permeate}}\operatorname{arctanh}\left(\sqrt{\frac{P_{final}}{P_{permeate}}}\right)\right\} \times \frac{Vl_m}{RT\Phi_0 e^{(-E/RT)}A_m}$$

Equation 7

As seen in the equation, to reduce the pressure from $P_{initial}$ to $P_{final}$, the time can be reduced by increasing the membrane 18 surface area per unit sampling vessel volume, increasing the temperature or decreasing the thickness of the membrane. The temperature effect correlates both due to increased permeability in the membrane but also due to the lower amount of gas that can be entrained in the vessel at a constant initial pressure at higher temperatures.

Using Equation 7, the hydrogen permeability could be correlated with the membrane sampling device. At 250° C., the time needed to reduce the pressure by 40 psia (from about 165 psia) was 5 minutes. With these numbers as input, the permeability was estimated to $$\Phi(250° \text{ C.}) = 7.7 \times 10^{-5} \text{ mol/m}^2, \text{Pa}^{0.5}, \text{s}$$

which correlates well with literature data for dense Pd membranes. In an example to concentrate the impurities in the hydrogen by a factor of 10 times, sampling occurs at a pressure of 450 psia while the retentate pressure is reduced to 45 psia. In this example, the vessel is at 250° C. and the hydrogen permeates to ambient pressure (Ppermeate). Under those reference conditions and given our current membrane and reactor dimensions (V=500 cm$^3$, $A_m$=38 cm$^2$), the estimated time to concentrate the sample would be approximately 23 minutes.

Figure 7:
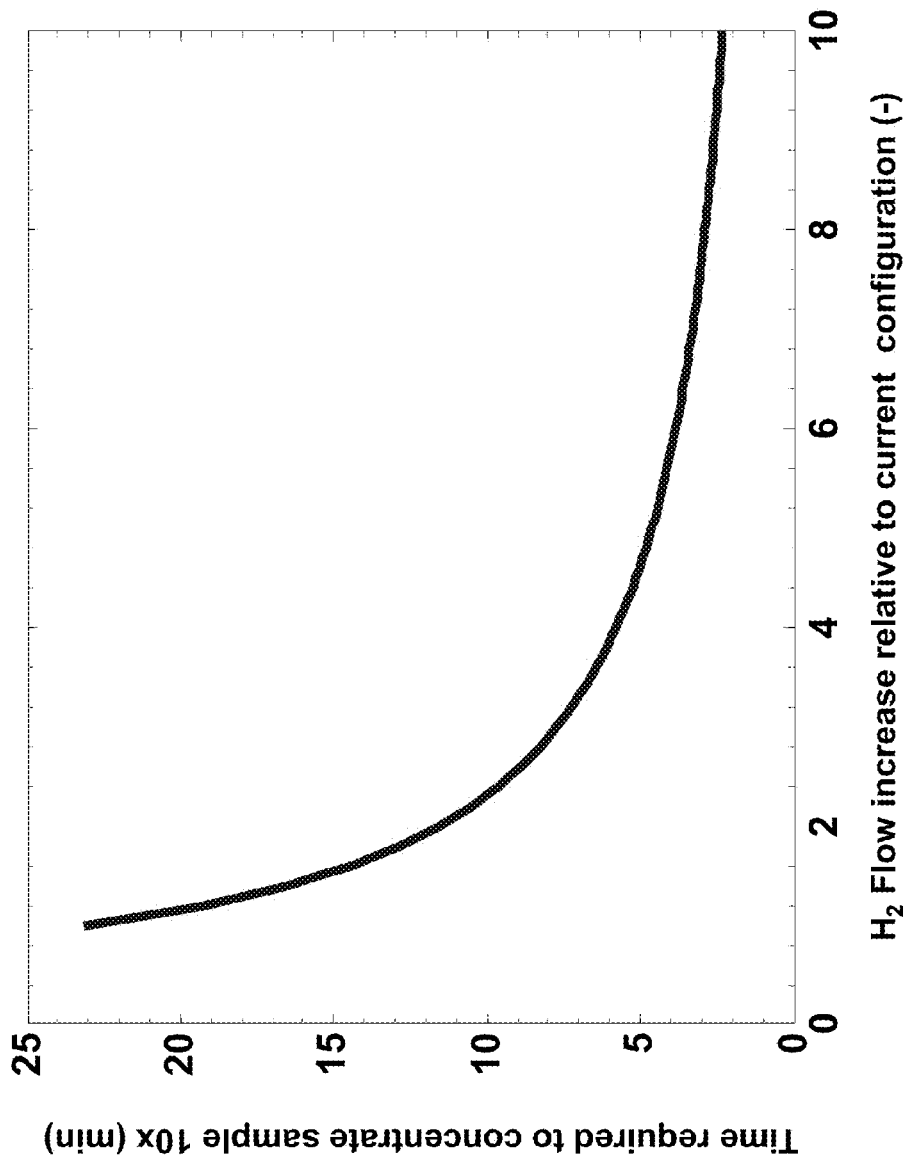
FIG. 7 depicts how the time required to concentrate a sample by a factor of ten can be reduced from 23 minutes to less than 3 minutes if the hydrogen flow through the permeation membrane can be increased ten-fold from the present value.

FIG. 7, shows how the impurity enrichment time can be reduced relative to the current set-up. If the hydrogen flow rate increases by a factor of 4, (e.g, by increasing the membrane surface area to more than 150 cm$^2$) the time to concentrate the sample can be reduced to about 5 minutes. A tenfold increase in area would correspondingly decrease the time to less than 3 minutes. Increasing the surface area to reduce the time is naturally associated with a cost factor. However, there are many combinations available, through the algorithms presented supra, to increase the hydrogen permeation rate where variations in temperature, membrane thickness and surface area can be combined to obtain the desired impurity enrichment time.

Impurity Enrichment by Adsorption Detail

Figure 2A:
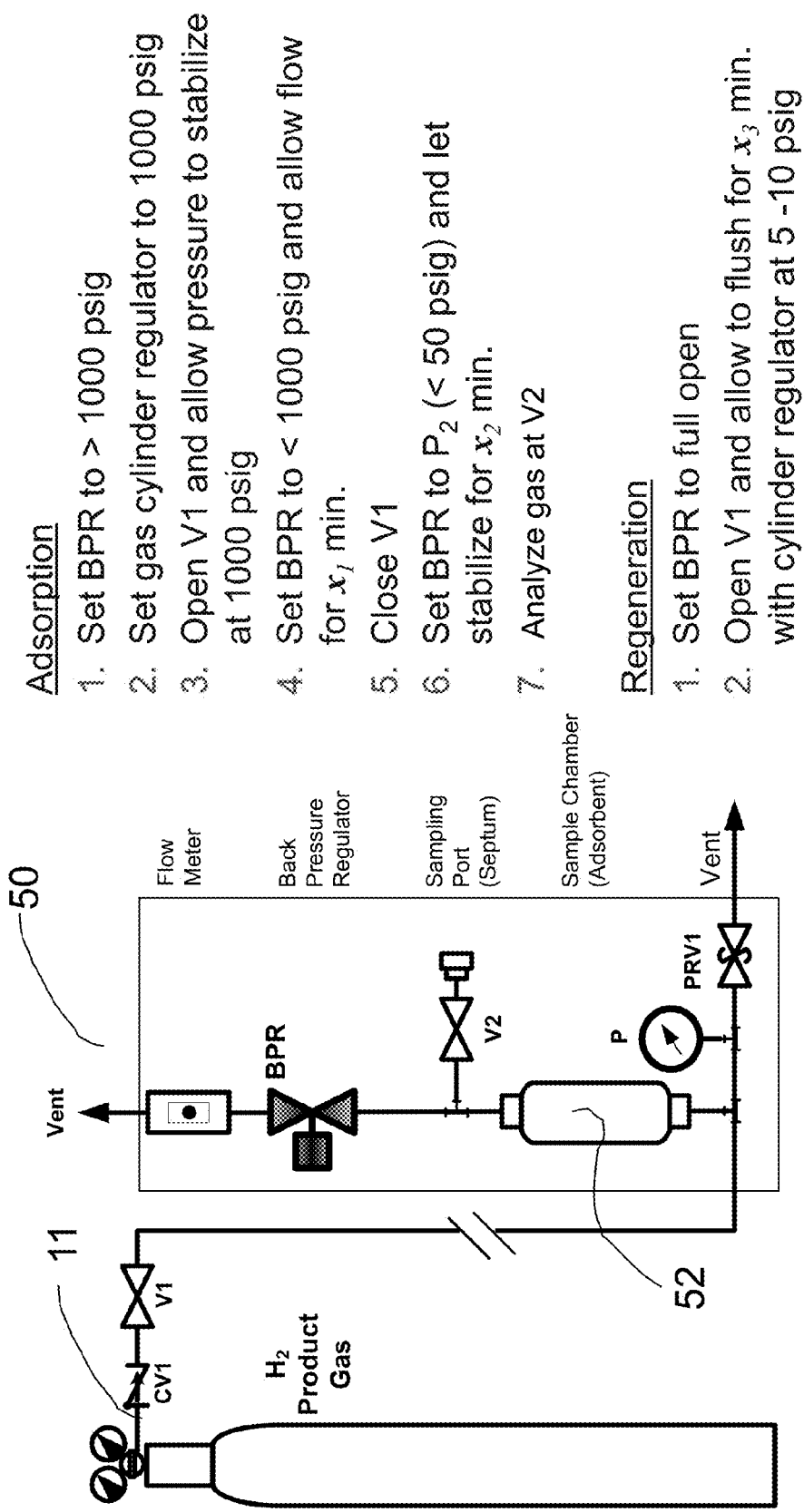
FIGS. 2A-B depict schematics of two embodiments of an adsorbent-based impurities adsorbing gas sampler.
Figure 2B:
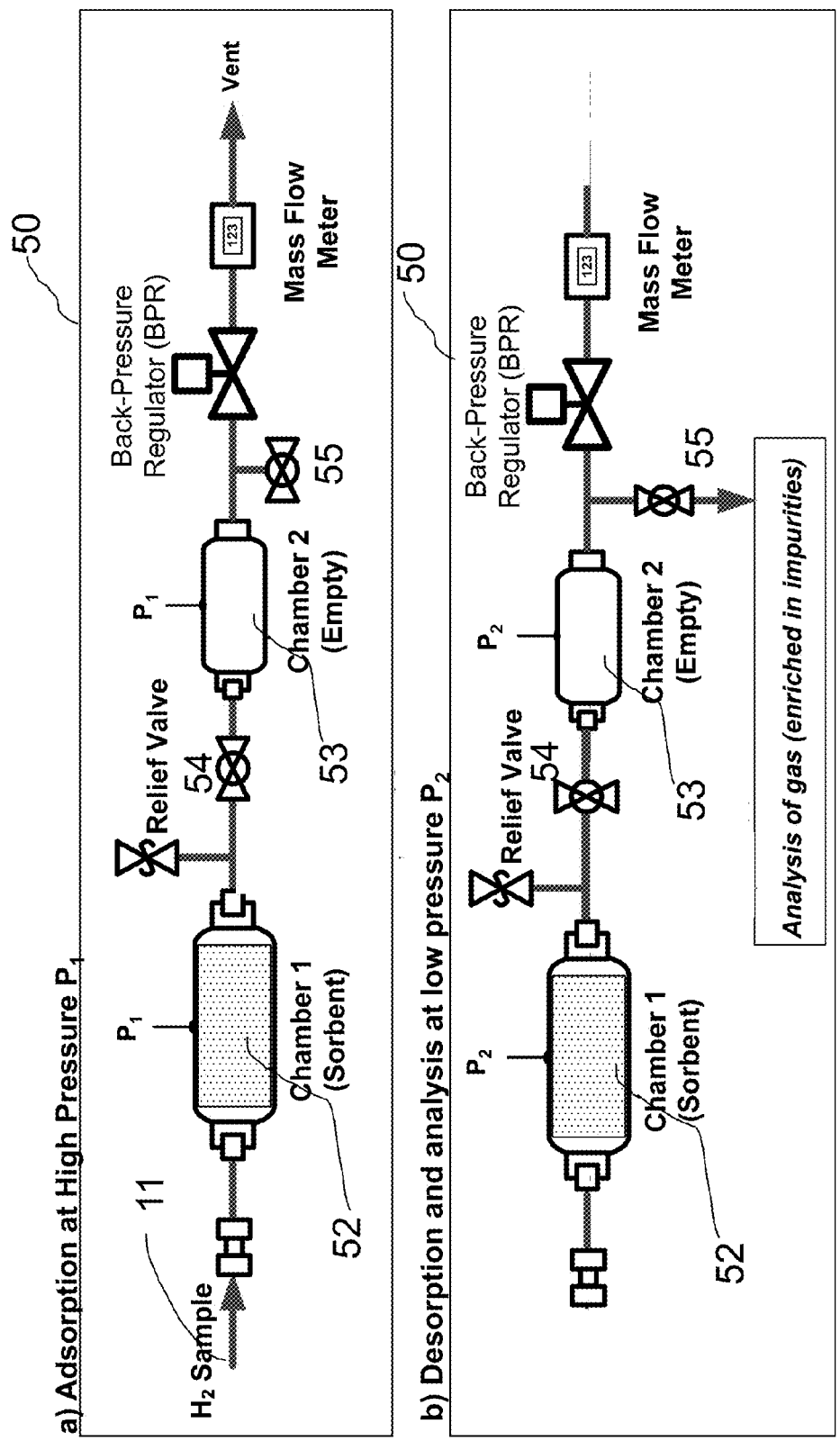

Alternative embodiments of the invention are shown in FIGS. 2A and 2B, designated as element 50. These figures depict apparatuses designed to concentrate impurities through the use of adsorption of the impurities over time.

One of these embodiments shown in FIG. 2A consists of an apparatus wherein a specified amount of the hydrogen fuel 11 flows at high pressure over a bed 52 of sorbents selected to preferentially adsorb the impurities. After a predetermined amount of fuel contacts the sorbents, the impurities are desorbed at a lower pressure, which in turn produces a sample (desorbed gas) with a higher concentration of impurities. A salient feature of the desorption step is that the adsorbed impurities are released as a result of lower total pressure and not by the lowering of partial pressure which is the result of flow of a carrier gas used in gas chromatograph scenarios.

The concentration factor is a function of a number of parameters such as the amount of high pressure hydrogen flowed through the bed, the initial and final pressures, the type of sorbent, and temperature. This process takes advantage of the differences in the sorption affinities (adsorption isotherms) of hydrogen and the impurities for one or more sorbents.

An alternative of the apparatus as shown in FIG. 2B is now extended with an empty vessel 53 in series with the vessel containing the adsorbents 52. The gas exiting bed 52 flows through the empty vessel 53 before being vented. After the predetermined amount of fuel contacts the sorbents, the pressure is reduced to ambient or close to ambient pressure (1-10 psig). The impurities are desorbed at a lower pressure, which in turn produces a sample (desorbed gas) with a higher concentration of impurities in vessels 52 and 53. The valve 54 is closed isolating 52 from 53 and the gas enriched in impurities is analyzed from vessel 53 through a sampling port 55. The advantage of collecting and analyzing the desorbed impurities in a separate vessel isolated from the primary adsorption vessel 52 is that the gas composition remains invariant regardless of pressure changes. The down stream, empty vessel 53 provides a means for storing or otherwise sequestering the enriched impurities for analysis, either simultaneous with the production of the enriched sample, at scheduled analysis times, or at will by, for example, fuel purity inspectors.

Generally, this contamination detection method, involves two principal stages:

1). The whole system is flushed with the hydrogen sample gas at low pressure, i.e. ambient pressure or lower. This purges gas from previous analysis also serves as a regeneration step of the sorbent bed.

2.) Adsorption occurs at high pressure (up to 12000 psig and preferably between 100 and 5000 psig) during which preferentially adsorbed species are picked up from the gas phase; and 3.) Desorption—where adsorbed species are removed from the sorbent to the gas-phase and the enriched gas is analyzed at near ambient pressure.

Figure 3:
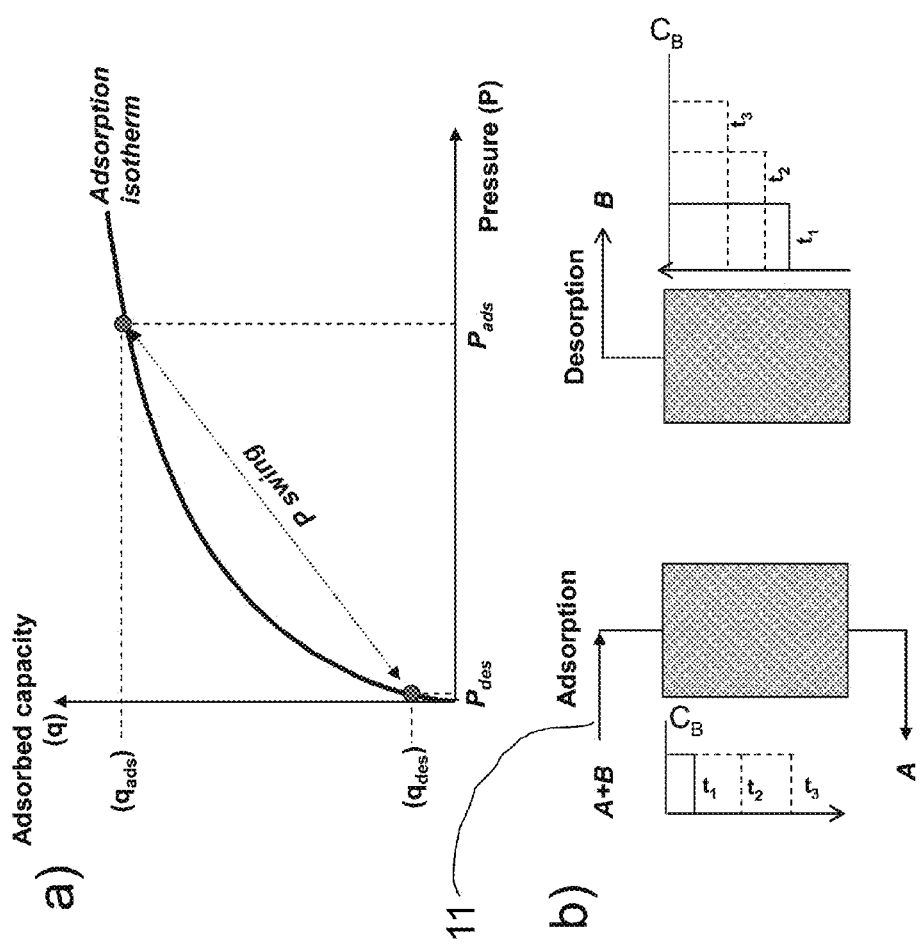
FIG. 3 depicts the working load of adsorbent at varying pressures and a schematic representation of a bed during adsorption and desorption of species A+B.

The Adsorption/Desorption cycle follows the Pressure-Swing Adsorption (PSA) methodology. The general concept of pressure swing adsorption purification is shown schematically in FIG. 3. If the process operates at isothermal conditions, the useful adsorption capacity is the difference in loading between the adsorption and desorption steps on the adsorption isotherm. By "swinging" the pressure, the process cycles between a production and regeneration mode.

FIG. 3B shows schematically the movement of the concentration profiles in the bed during these alternating pressure modes. During adsorption, the feed 11 is terminated when the more strongly adsorbed species (B) "breaks through" the bed and exits with the pure product A. This step is conducted at high pressure. During regeneration, the preferentially adsorbed species B is desorbed by reducing the pressure, which then leaves the bed in a concentrated form relative to the feed.

Differences in gas-phase concentrations during the adsorption/desorption cycle for the preferentially adsorbed species, are utilized in the invented adsorption method 50 shown in FIG. 2. This technique allows the enrichment of most gases (with the exception of helium) present in hydrogen, since hydrogen has a very low affinity to adsorb.

Preferably, to ensure repeatability, the beds are regenerated before each sorption/desorption cycle. This is done by purging the bed with the (next) feed gas at ambient pressure to remove the non-hydrogen species in the void space of the sample chamber 52.

The adsorption isotherm for a single species shows a non-linear behavior as function of pressure (FIG. 3A). For dilute species, the adsorption capacity will be linear. Thus, the enrichment factor will be the same regardless of the sample concentration. The enrichment factor for CO is 12.4, that is if the original sample contains 10 ppm of CO, the enriched gas will contain CO at 124 ppm. If the sample now is 100 ppm; however, the CO in the enriched gas will not be at 1240 ppm but diluted to about 1238. The higher the original concentration, the lower will the enrichment factor be, i.e. a certain error from the dilute species enrichment factor.

Also, adsorption of a multicomponent mixture reflects a competition of all species for the adsorption sites. This effect is shown in Equation (8 as a function of fractional coverage.

$$\theta_A = \frac{K_A P_A}{1 + K_A P_A + K_B P_B + ...},$$

$$\theta_B = \frac{K_B P_B}{1 + K_A P_A + K_B P_B + ...}, ...$$

Equation 8

Equation 8 is an extension of the single component Langmuir adsorption isotherm for a multi-component system. (A, B, etc., denote the adsorbed species in the gas.) For a given temperature and sorbent selection (which determines $K_A$, $K_B$ ...), the quantity of each species that will be adsorbed at a given partial pressure will be lower than the single component adsorption at the same pressure. Under such conditions, the adsorption of a particular species will also vary depending on the partial pressure of all other species in the sample gas. As noted supra, the adsorption isotherm for dilute moieties follows a linear relationship (Henry's law region). Under such conditions, the adsorption isotherm in a multicomponent mixture can be decoupled and independent of the other species in the mixture. In this case, Equation 8 is reduced to Equation 9, to wit:

$$\theta_A = K_A P_A, \theta_B = K_B P_B$$

Equation 9

As pressure and total impurity concentrations in the sample feed start to increase, the adsorption will start to deviate from the ideal case given in Equation 9 and become dependent on all concentrations in the mixture, Equation 8.

Example 1

Based on a model for pressure swing-adsorption developed by the inventors, and disclosed in Papadias, D.; et al., Hydrogen quality for fuel cell vehicles—A modeling study of the sensitivity of impurity content in hydrogen to the process variables in the SMR-PSA system. International Journal of Hydrogen Energy 34, 6021-6035 the entirety of which is incorporated by reference, a numerical experiment was performed to investigate the range of concentrations and pressures for which the adsorption process deviates from linearity.

Figure 4:
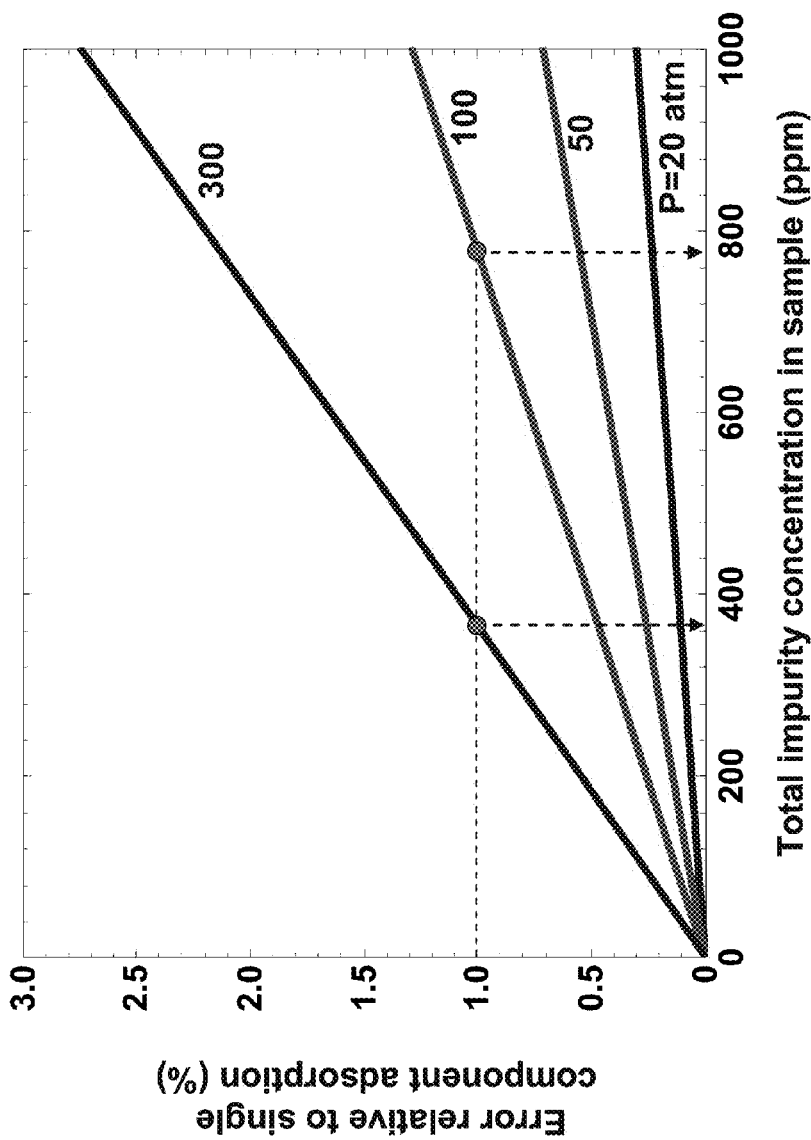
FIG. 4 depicts the error in a single component enrichment (CO=2 ppm) relative to when the feed mixture contains other species ($N_2$, CO and $CH_4$ at equal concentration)

A gas containing 2 ppm of CO in hydrogen was fed to a vessel filled with activated carbon after which the CO was adsorbed at various pressures. After saturation, the pressure was reduced, allowing the CO to desorb, thereby causing the CO in the gas-phase to become enriched. The same calculation was repeated but adding $N_2$, $CO_2$ and $CH_4$ at equal concentrations in the feed (a total concentration of 300 ppm means that each species in the feed is 100 ppm). When the pressure was reduced, the error in the CO enrichment relative to single component adsorption was compared, and the results are shown in FIG. 4. As the concentration of impurities and pressure in the feed increase, the relative error increases. To maintain an error of say below 1 percent relative to the single component calibration curve, the total impurity concentration should not exceed 360 ppm when adsorbed at 300 atm. Alternatively, if the adsorption is restricted to 100 atm, the total impurity concentration can increase to almost 780 ppm for the same 1 percent error. Considering that the device is aimed to enrich the concentrations of impurities present in ppm and even ppb levels, a single component calibration curve can be used to determine the enrichment factor with negligible error as a function of pressure.

Figure 5:
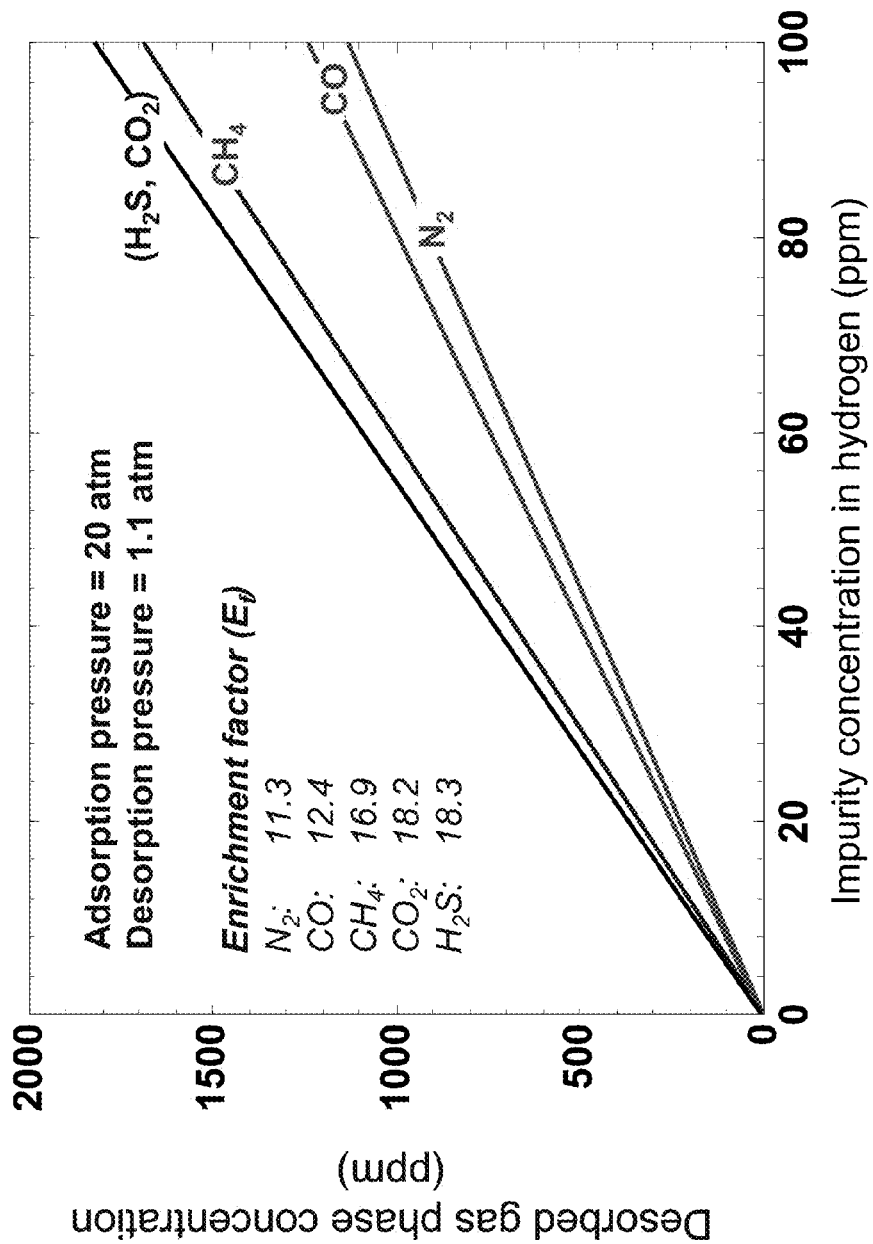
FIG. 5 depicts enrichment of single component mixture in hydrogen ($N_2/H_2$, $CO/H_2 CH_4/H_2$, $CO_2/H_2$ and $H_2S/H_2$) on activated carbon. The diluted species at various concentrations in the feed is adsorbed at 20 atm and desorbed at about 1 atm to achieve the higher concentration of the species in the gas phase.

Enrichment Factor ($E_f$):

The enrichment factor indicates how many times the impurities in the hydrogen feed can be concentrated in the gas-phase during an adsorption/desorption cycle. The enrichment factor depends on adsorbent selection, adsorption- and desorption-pressure, and is different for the different impurity species. FIG. 5, shows the calculated enrichment on activated carbon for five different single components in hydrogen where adsorption occurs at about 20 atm and the pressure is then released to about 1 atm to desorb or release the adsorbed species. Under these conditions, for example, it is seen that CO is concentrated in the final gas phase to 12.4 times the concentration of the CO in the original sample aliquot.

The increase in concentration achieved during the adsorption/desorption cycle is directly proportional to the original feed concentration and the slope is the enrichment factor. Since different species have different affinity to adsorb on various sorbents, the enrichment factor shows a variation for each species. $CO_2$ and $H_{2S}$ adsorbs more strongly on carbon than any of the other species and shows the highest enrichment factor ($E_f$=18). By contrast, the $N_2$ concentration on activated carbon shows the lowest enrichment factor of about 11.

Alternatively, if a polar sorbent like zeolite A was chosen as a adsorbent, the enrichment factor of CO and $N_2$ would increase by an additional 50% relative to activated carbon, without significantly changing the enrichment factor for $H_2S$. The polar nature of CO and $N_2$ molecules (permanent dipole and quadrupole moments) are responsible for these behaviors. The sorbent can therefore be tailored depending on the importance of the species to analyze.

Even at a moderate adsorption pressure of about 20 atm, the adsorption method significantly concentrates the trace impurities of the sample feed by a factor of almost 20. A higher enrichment factor is achieved by increasing the sampling pressure (the pressure of the hydrogen dispensed at the refueling nozzle is typically at least 425 atm, i.e., 6250 psig).

Figure 6:
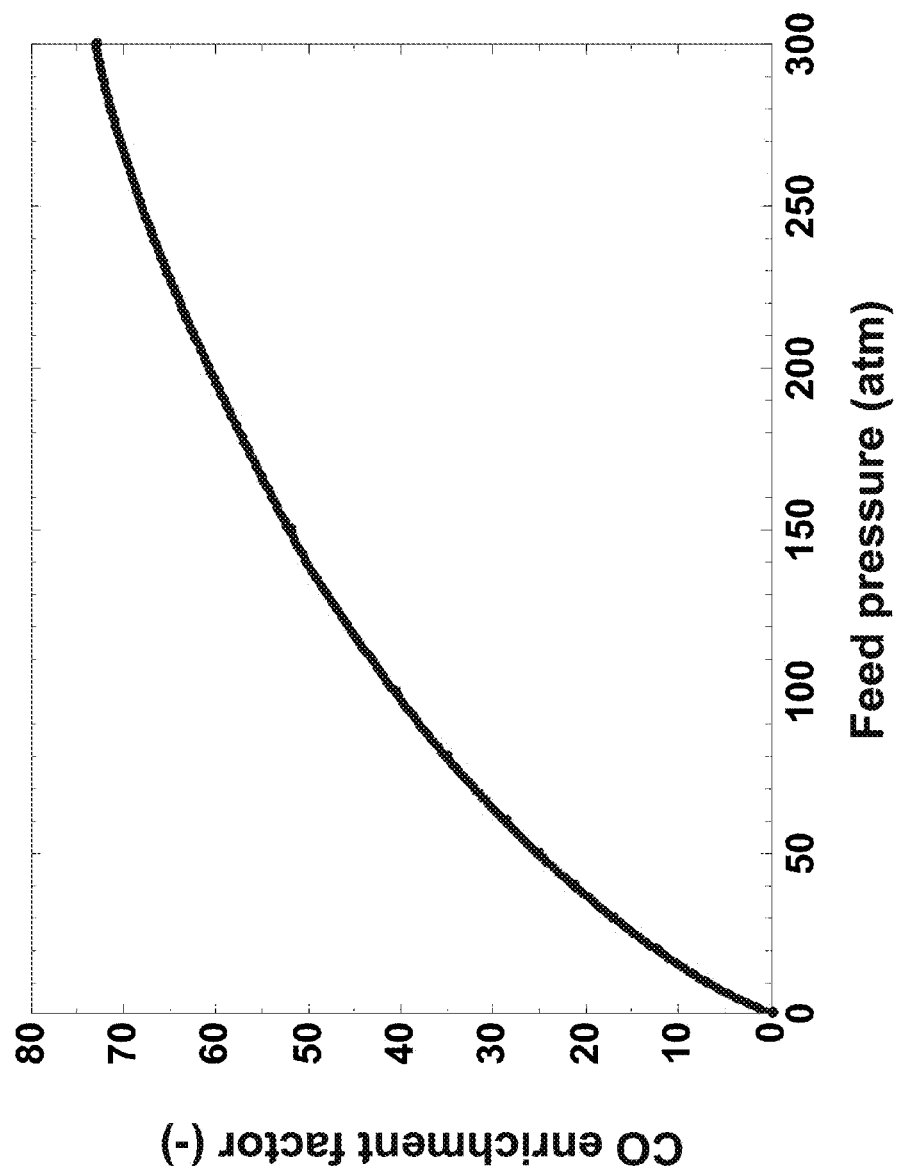
FIG. 6 depicts CO enrichment factor on activated carbon as function of feed pressure.

This is shown in FIG. 6, plotting the enrichment factor of CO on activated carbon as function of adsorption pressure (the desorption pressure is at 1.1 atm).

The enrichment factor increases with increasing pressure as anticipated and concentrates the CO by 70 times at 300 atm. It is also seen that the enrichment factor does not increase linearly with pressure, as given by Equation 9, but progressively levels off as the pressure increases. The reason for this behavior is that some hydrogen also adsorbs on the adsorbent. Since the partial pressure of hydrogen is essentially the same as the feed pressure, the effect of hydrogen adsorption becomes significant at elevated pressures. The adsorption isotherm as shown in Equation 9 is actually dependant on the hydrogen pressure as follows, $$\theta_A = K_A P_A \rightarrow \frac{K_A P_A}{1 + P_{H_2}} \rightarrow K'_A P_A \qquad \text{Equation 10}$$

For low concentrations of impurities in hydrogen, the calibration curve for the enrichment factor will still be linear as a function of impurity concentration, but dependant on the adsorption pressure. Preferably, adsorption of the hydrogen gas sample is made at the same pressure at which the calibration has been obtained.

One potential risk with adsorbents is that they can lose adsorption capacity with time. Thermal, mechanical and pressure cycling are possible causes that can reduce the effectiveness of the sorbent. However, modest thermal cycling can be beneficial to further increase the enrichment factor, i.e. combined desorption and heating.

Morphological changes to the adsorbents can result from pressure cycles, especially if the pressure swing is very high. This effect is mitigated by reducing the pressure swing (which will reduce the moles of gas that can be adsorbed, i.e., capacity) and by increasing the loading of the sorbents. If an enrichment factor of 10 to 20 is sufficient, then the pressure swing can be limited to 20 atm.

Example 2

Membrane Concentrator Data

Turning to FIG. 1D, a high-pressure $H_2$ sampling vessel, 16, rated for up to 1500 psig at room temperature, is used to collect a sample of hydrogen from a hydrogen gas source 11 for analysis. The sampling vessel 16 is connected to a second chamber, or volume, heretofore designated as the impurity concentrating vessel 12. In this particular example, the concentrating vessel 12 contains a Pd-alloy membrane tube. Hydrogen transport through the membrane is activated by raising the temperature of the membrane tube. The removal of hydrogen from the chamber results in higher impurity concentrations and a lower chamber pressure. The concentrating vessel obviates the need for separating or fractionating the trace species to be analyzed. No temperature cycle is needed to desorb the impurities. Also, desorption occurs without application of a high vacuum, which otherwise would make the process unsuitable for regular analysis in the field.

A series of tests were conducted with the sample gas (0.2% each of $N_2$, CO, $CO_2$ and $CH_4$ in $H_2$) being collected in the sample retaining vessel 16 at 700 psig. This gas was slowly bled into the concentrating vessel 12 (maintained at 150-200 psig) where the hydrogen was permeated out through the Pd-alloy membrane heated to 250° C. This process continued until the pressures in both chambers dropped to 32 psig. After cooling the concentrating vessel 12 to ambient temperature, the pressure was further reduced to about 20 psig and the residual gas therein was analyzed using a gas chromatograph.

Based on the initial and final pressures of the gases in the sample retaining vessel 16 and the impurity concentrating vessel 12, the theoretical concentration multiplier was calculated For the two experiments conducted (Runs A and B) an enrichment factor in the order of at least 30 were achieved. The analytical multipliers (enrichment factors), defined as the ratio of the final to initial concentrations of each species, were calculated from the gas analyses and compared to the theoretical (predicted) enrichment factor, see Table 1, below. The analytical (measured) enrichment factors were found to match the predicted values. The enrichment factor variability for each individual species was smaller than four percent and was within the limits of uncertainty of the analytical equipment (gas chromatograph) to measure the concentrations. This indicates that the loss of species due to adsorption or chemical reaction was negligible.

TABLE 2

Actual Versus Theoretical Enrichment Factors for Pd-based membranes

| Test (M1) | Run A | Run B |
| --- | --- | --- |
| Pressure (Initial/Final), psig | 700/19.2 | 700/19.8 |
| Theoretical Enrichment Factor, $E_T$ | 32.3 | 31.8 |
| Membrane Temperature, ° C. | 250 | 250 |
| Analytical Enrichment, $E_A$: $N_2$ | 33.4 | 32.9 |
| Variation from Predicted Value | +3.2% | +3.7% |
| Analytical Enrichment, $E_A$: $CH_4$ | 31.4 | 31.3 |
| Variation from Predicted Value | −2.8% | −3.3% |
| Analytical Enrichment, $E_A$: CO | 32.5 | 32.4 |
| Variation from Predicted Value | +0.5% | +2.1% |
| Analytical Enrichment, $E_A$: $CO_2$ | 31.5 | 31.1 |
| Variation from Predicted Value | −2.5% | −2.0% |

Table 2 shows the results of two repeated tests to enrich a gas sample containing 0.2% each of $N_2$, CO, $CO_2$ and $CH_4$ in $H_2$. Enrichment factors of more than 30 were achieved as predicted when the sample gas was collected at 700 psig and the final pressure was reduced to ~20 psig. Enriched gas concentrations of the impurities were as follows: $N_2$=6.90±0.018, $CH_4$=6.68±0.004, CO=6.76±0.008, $CO_2$=6.60±0.014.

Example 3

Adsorption Data

To demonstrate the proof-of-concept, an experimental apparatus was set up. FIG. 2B shows the schematic of the apparatus. In an embodiment of the adsorbent-featured system, the sorbent chamber 52 (having a volume of 50 mL) was packed with about 24 g of activated carbon (provided by Norit, Inc) while a downstream chamber 53 (10 mL) was left empty. Hydrogen gas containing 0.2% of each of the impurity species $N_2$, CO, $CH_4$, and CO, was passed through the two vessels at high pressure (700 psig) to adsorb the impurities.

Of the four impurity species, the sorbent was found to equilibrate (i.e., reach its capacity for adsorbing) successively to the concentrations of nitrogen, carbon monoxide, methane, and carbon dioxide in the feed gas. This sequence reflects the adsorption capacity of the carbon for the species, i.e., the carbon has a greater capacity for adsorbing $CO_2$ than the other species. Approximately 200 liters of gas (containing 0.2% each of N2, CO, CH4, and CO2) ensured equilibration with all the species.

Figure 8:
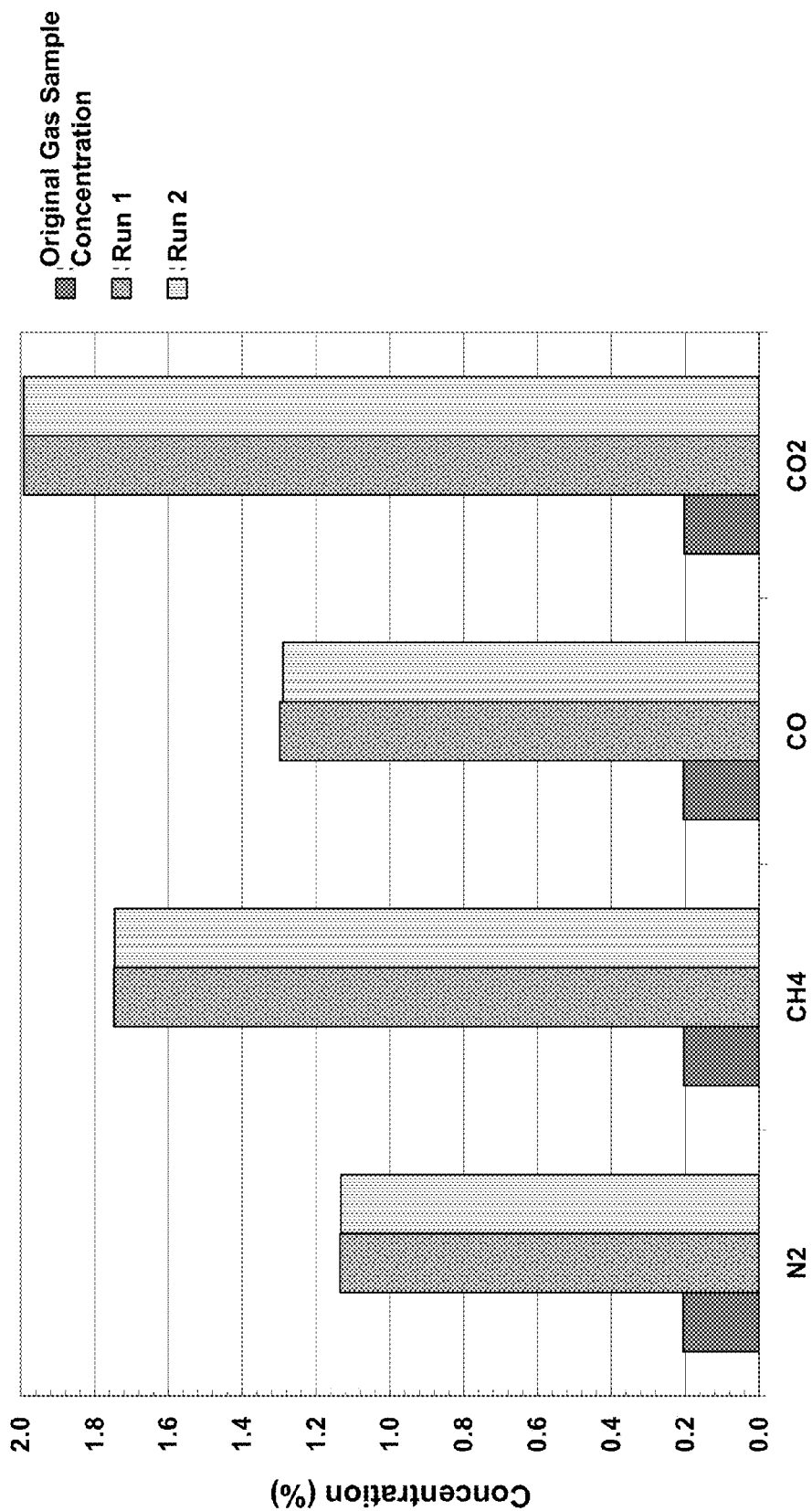
FIG. 8 is a graph showing impurity concentrations in a retention chamber, in accordance with features of the present invention.

The impurities were subsequently desorbed by reducing the pressure in the system to 6 psig. The gases in both chambers were analyzed using a micro-GC. The impurity concentrations from the gas in the downstream chamber 54 are shown in FIG. 8, where the concentrations of each species were considerably higher than that in the original gas. The enrichment factors (ratio of final to initial concentration) ranged from about 5.5 for $N_2$ to 9.8 for $CO_2$.

The data for two experiments, conducted on two different days, show very good agreement, indicating repeatability of the enrichment process.

The results suggest that as long as the total flow is sufficiently high to equilibrate the species with the adsorbent loading, the enrichment factors for the species are almost independent of the total flow. The very small standard deviations are indicative of the repeatability of the process.

In summary, embodiments of the invention address the difficulty of the analysis of a sample, namely the very low concentrations of the species of interest, and enriching their concentration by (1) removing the hydrogen, and, in an alternative embodiment (2) trapping and collecting the impurities. These embodiments do not require the development of more sensitive detectors and analytical equipment, a strategy that is not well suited to the cost-sensitive hydrogen fueled vehicles and refueling infrastructure, businesses that are in the early stages of development.

The invention also provides a means for establishing the enrichment factor and therefore the concentration of the species in hydrogen samples. The invented method thus limits the possible errors that can result from, for example, side reactions at elevated temperatures, loss of adsorption capacity, and so forth. Upon enriching the collected gas samples, the enriched gas can be analyzed with gas chromatograph and mass spectrometers.

The invention is designed for use with the high pressure hydrogen feeds available at hydrogen gas production facilities or at the dispensing nozzle. Further, the invention is capable of storing the enriched sample, and is not part of any analytical equipment in that the invention serves as a means to produce and store enriched aliquots indefinitely until analysis is commenced. The enriched fluid can subsequently be injected into an analytical device.

Other unique aspects of the invention are that it is capable of enrichment by several orders of magnitude through sizing of the chambers and varying the initial and final pressures of sample fluids; that it uses membranes that adsorb the target gas (e.g., hydrogen) whereby the hydrogen molecule is split into atoms which are carried through the metallic lattice of the membrane. As such the impurities are enriched in the raffinate stream. The invented method and device is not affected by adsorption of the trace impurities, because any impurities adsorbed on the membrane are removed during the regeneration and/or purging steps of the cyclic (batch process.

As used herein, an element or step recited in the singular and preceded with the word "a" or "an" should be understood as not excluding plural said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting, but are instead exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the terms "comprising" and "wherein." Moreover, in the following claims, the terms "first," "second," and "third," are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

The embodiment of the invention in which an exclusive property or privilege is claimed is defined as follows:

1. A batch method for enriching trace impurities in a first sample of a hydrogen gas for their further analysis, the method comprising:
   (a) sequestering the sample in an analytical chamber having a first volume $V_1$ at an initial pressure $P_{hi}$ between 1000 to 12000 psig wherein the first sample contains hydrogen gas and an unknown quantity of trace impurities;
   (b) transferring the sample to a second chamber having a second volume V2, the second chamber containing a hydrogen transport membrane;
   (c) increasing concentration of trace impurities in the second chamber relative to the hydrogen gas by removing primarily hydrogen from the second chamber through the transport membrane, thus reducing the pressure in the analytical chamber from the initial to a second pressure $P_{lo}$ which ranges from about 10 to 1000 psig, to form a raffinate stream containing hydrogen gas with a higher concentration of trace impurities, during a time period;
   wherein the time period for concentrating the sample is calculated on the basis of optimized membrane characteristics, comprising its thickness and permeance, with optimization of temperature within a temperature range of above 150° C. and below 350° C., and
   wherein the enrichment of trace impurities is proportional to the pressure ratio $P_{hi}/P_{lo}$ and the volume ratio $V_1/V_2$;
   (d) injecting the raffinate stream from the second chamber into an analytical device to reproducibly measure the concentration of the trace impurities, the steps a-d defining a cycle; and
   (e) purging the chamber after each cycle with a second sample of hydrogen gas at ambient temperature to remove any remaining trace impurities from the chamber.

2. The method as recited in claim 1 wherein the transport membrane contains palladium.

3. The method as recited in claim 1 wherein the transport membrane does not contain palladium.

4. The method as recited in claim 1 wherein the analytical device further comprises a gas chromatograph.

5. The method as recited in claim 1 wherein the analytical device further comprises a mass spectrometer.

6. The method as recited in claim 1 wherein the analytical device further comprises a portable device.

7. The method as recited in claim 1 wherein the second chamber is maintained at ambient temperature after transferring and storing the raffinate stream.

8. A batch method for enriching trace impurities present in a sample of a hydrogen gas for their further analysis, the method comprising:
   a) directing the sample to a system comprising a first volume $V_1$ and a second $V_2$ at a first pressure $P_{hi}$, wherein the first volume contains a sorbent;
   b) allowing the trace impurities to preferentially adsorb to the sorbent while allowing the hydrogen gas to leave the first volume;
   c) stopping the flow of sample gas to the system;
   d) decreasing the pressure from the system to a second pressure $P_{lo}$ that is lower than the first pressure, thereby causing desorption of the trace impurities from the sorbent and forming a desorbed gas in the first volume $V_1$ and second volume $V_2$;
   e) isolating $V_1$ from $V_2$;
   f) analyzing the desorbed gas in $V_2$; and
   g) regenerating the sorbent.

9. The method as recited in claim 8 wherein enrichment occurs at impurity concentrations where Henry's law is valid.

10. The method as recited in claim 9 wherein the impurities are present at concentrations up to about 100 ppm.

11. The method as recited in claim 8 wherein the analytical device determines the amount of the sample which contacted the sorbent material.

12. The method as recited in claim 8 wherein the impurities are present in the sample at less than 1000 ppm.

13. The method as recited in claim 8 wherein a concentration of a first impurity A and a second impurity B is determined via equation $\theta_A = K_A P_A$, $\theta_B = K_B P_B$, ... wherein $K_A$ and $K_B$ is the adsorption constant for impurities A and B respectively, $P_A$ is the partial pressure of impurity A, and $P_B$ is the partial pressure of impurity B.

14. The method as recited in claim 8 wherein $P_{hi}$ is up to 4400 psig.

15. The method as recited in claim 8 wherein regeneration occurs when $V_1$ and $V_2$ are purged with hydrogen gas at ambient pressure or lower.

16. A batch method for enriching trace impurities present in a sample of a hydrogen gas, wherein the impurities have a concentration of about 1000 ppm or less, the method comprising:
   a) directing the sample to a system comprising a first volume $V_1$ and a second $V_2$ at a first pressure $P_{hi}$ which is below 4400 psig, wherein the first volume contains a sorbent;
   b) allowing the trace impurities to preferentially adsorb to the sorbent while allowing the hydrogen gas to leave the first volume;
   c) stopping the flow of sample gas to the system;
   d) decreasing the pressure from the system to a second pressure $P_{lo}$ that is lower than the first pressure, thereby causing desorption of the trace impurities from the sorbent and forming a desorbed gas in the first volume $V_1$ and second volume $V_2$;
   e) isolating $V_1$ from $V_2$;
   f) determining the weight of the impurities in the desorbed gas in $V_2$; and
   g) regenerating the sorbent.

17. The method as recited in claim 16 wherein initial concentration of the impurities is 100 ppm or less and the step of determining the weight of a first impurity A and a second impurity B is via equation $\theta_A = K_A P_A$, $\theta_B = K_B P_B$, ... wherein $K_A$ and $K_B$ is the adsorption constant for impurities A and B respectively, $P_A$ is the partial pressure of impurity A, and $P_B$ is the partial pressure of impurity B.

18. The method as recited in claim 16 wherein regeneration occurs when $V_1$ and $V_2$ are purged with hydrogen gas at ambient pressure or lower.

\* \* \* \* \*

UNITED STATES PATENT AND TRADEMARK OFFICE
CERTIFICATE OF CORRECTION

| | | |
|---|---|---|
| PATENT NO. | : 8,778,694 B2 | Page 1 of 1 |
| APPLICATION NO. | : 12/835614 | |
| DATED | : July 15, 2014 | |
| INVENTOR(S) | : Shabbir Ahmed et al. | |

It is certified that error appears in the above-identified patent and that said Letters Patent is hereby corrected as shown below:

In the claims:

On column 16, line 34, change "V2" to -- $V_2$ --

Signed and Sealed this
Fourteenth Day of October, 2014

Michelle K. Lee
*Deputy Director of the United States Patent and Trademark Office*